United States Patent
Drugeon et al.

(10) Patent No.: US 11,470,946 B2
(45) Date of Patent: Oct. 18, 2022

(54) ASSEMBLY FOR PACKAGING AND APPLYING A COSMETIC PRODUCT COMPRISING AT LEAST ONE VOLATILE SOLVENT

(71) Applicant: L'OREAL, Paris (FR)

(72) Inventors: Lionel Drugeon, La Garenne Colombes (FR); Eric Caulier, Ferrieres (FR); Jean-Marc Lebrand, Pantin (FR); Denis Befve, Arras (FR)

(73) Assignee: L'OREAL, Paris (FR)

( * ) Notice: Subject to any disclaimer, the term of this patent is extended or adjusted under 35 U.S.C. 154(b) by 590 days.

(21) Appl. No.: 15/576,765

(22) PCT Filed: May 25, 2016

(86) PCT No.: PCT/EP2016/061853
§ 371 (c)(1),
(2) Date: Nov. 24, 2017

(87) PCT Pub. No.: WO2016/189061
PCT Pub. Date: Dec. 1, 2016

(65) Prior Publication Data
US 2018/0295969 A1      Oct. 18, 2018

(30) Foreign Application Priority Data
May 26, 2015   (FR) ...................................... 1554674

(51) Int. Cl.
*A45D 40/26*     (2006.01)
*A46B 9/02*      (2006.01)
(Continued)

(52) U.S. Cl.
CPC ......... *A45D 40/267* (2013.01); *A45D 40/262* (2013.01); *A45D 40/265* (2013.01);
(Continued)

(58) Field of Classification Search
CPC .. A45D 40/267; A45D 40/262; A45D 40/265; A45D 2200/1018; A45D 34/04;
(Continued)

(56) References Cited

U.S. PATENT DOCUMENTS 4,527,575 A * 7/1985 Vasas ..................... A45D 40/26
                                                132/218
6,076,985 A * 6/2000 Gueret ................. A45D 34/046
                                                401/121
(Continued)

FOREIGN PATENT DOCUMENTS

EP        0872193 A1    10/1998
EP        1129641 A2     9/2001
(Continued)

OTHER PUBLICATIONS

International Search Report dated Jul. 27, 2016, in PCT/EP2016/061853, filed May 25, 2016.

*Primary Examiner* — Rachel R Steitz
(74) *Attorney, Agent, or Firm* — Oblon, McClelland, Maier & Neustadt, L.L.P.

(57) ABSTRACT

The present invention relates to an assembly for packaging and applying a cosmetic product comprising at least one volatile solvent, said packaging and application assembly comprising an applicator comprising an applicator member having a main body bearing a set of protruding application elements that define between one another a plurality of spaces for loading and applying the cosmetic product, characterized in that at least some of the spaces for loading and applying cosmetic product are delimited by at least one surface produced from an open-cell porous material that can selectively absorb some of the volatile solvent of the cosmetic product.

5 Claims, 6 Drawing Sheets

(51) Int. Cl.
- *A61Q 1/10* (2006.01)
- *A61K 8/30* (2006.01)
- *A46B 11/00* (2006.01)
- *A46B 3/18* (2006.01)

(52) U.S. Cl.
CPC .............. *A46B 3/18* (2013.01); *A46B 9/021* (2013.01); *A46B 11/0068* (2013.01); *A61K 8/30* (2013.01); *A61Q 1/10* (2013.01); *A45D 2200/1018* (2013.01); *A46B 2200/1053* (2013.01); *A61K 2800/87* (2013.01)

(58) Field of Classification Search
CPC .. A45D 34/042; A45D 34/043; A45D 34/045; A45D 34/046; A45D 40/26; A45D 40/264; A46B 3/18; A46B 9/021; A46B 11/0068; A46B 2200/1053; A46B 2200/106; A46B 2200/1046; A61K 8/30; A61K 2800/87; A61Q 1/10
USPC ........... 132/200, 218, 313, 317, 202; D28/7; D4/128; 401/126, 128, 130, 122
See application file for complete search history.

(56) References Cited

U.S. PATENT DOCUMENTS

| | | | |
|---|---|---|---|
| 6,386,781 | B1 | 5/2002 | Gueret |
| 8,210,763 | B2* | 7/2012 | Gueret .................. A45D 40/265 401/129 |
| 2001/0046406 | A1 | 11/2001 | Schrepf |
| 2002/0054783 | A1 | 5/2002 | Gueret |
| 2002/0164192 | A1* | 11/2002 | Gueret .................. A46D 1/0261 401/129 |
| 2007/0231051 | A1* | 10/2007 | Flores ..................... A61P 31/02 401/132 |
| 2007/0246058 | A1 | 10/2007 | Bodelin |
| 2009/0071499 | A1* | 3/2009 | Wyatt ..................... A46B 9/028 132/218 |
| 2015/0182005 | A1* | 7/2015 | Pires ..................... A45D 34/046 401/122 |
| 2015/0359317 | A1* | 12/2015 | Limongi ................. A45D 40/20 132/200 |

FOREIGN PATENT DOCUMENTS

| | | |
|---|---|---|
| EP | 1847254 A1 | 10/2007 |
| GB | 2146520 A | 4/1985 |

* cited by examiner

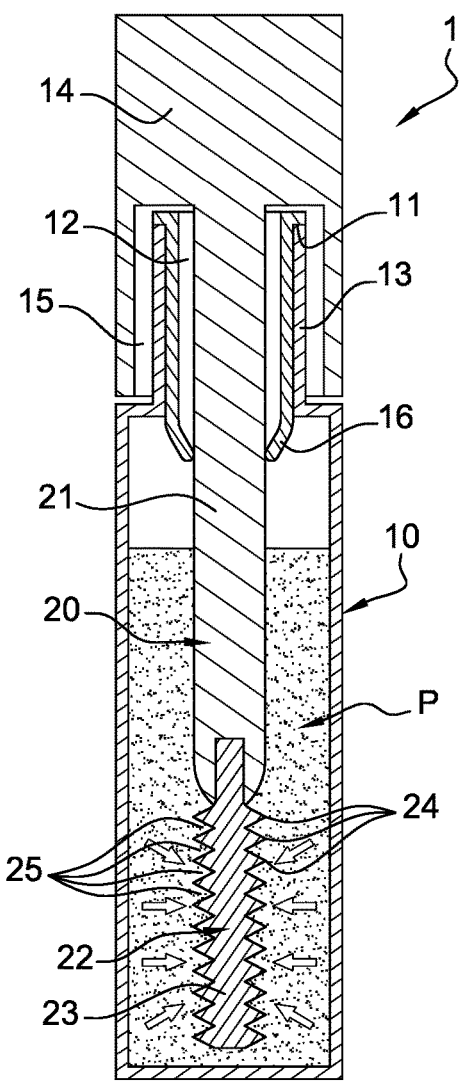
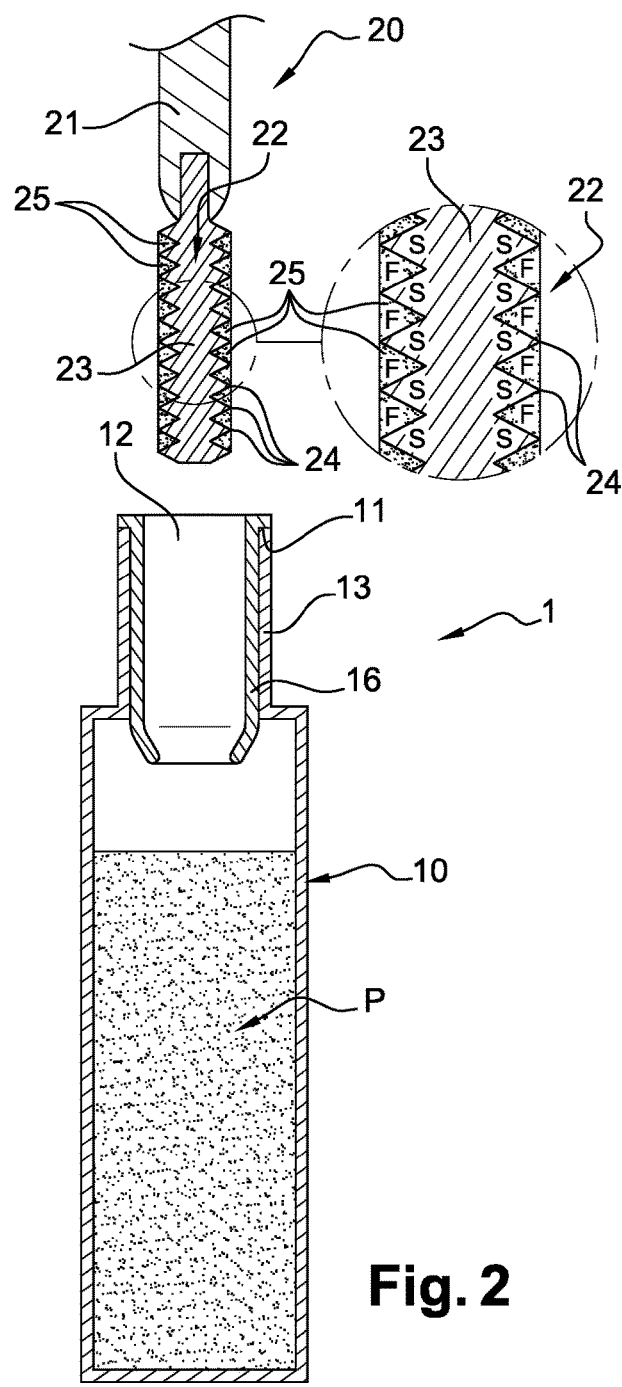
Fig. 1
Fig. 2

ASSEMBLY FOR PACKAGING AND APPLYING A COSMETIC PRODUCT COMPRISING AT LEAST ONE VOLATILE SOLVENT

The present invention relates to an assembly for packaging and applying a cosmetic product comprising at least one volatile solvent.

The packaging and application assembly is intended more particularly for the application of a cosmetic product to keratin fibres, and notably for the application of mascara to eyelashes.

The expression "cosmetic products" is understood to mean any product as defined in Regulation (EC) No 1223/2009 of the European Parliament and Council of 30 Nov. 2009 relating to cosmetic products.

A cosmetic product intended to be applied to keratin fibres, such as a mascara, generally comprises waxes and film-forming agents that tend to thicken the product and give it a pasty consistency. The same goes for other types of cosmetic products such as glosses, varnishes and foundations.

In order to allow and facilitate its application, such a cosmetic product is packaged in a container with a volatile solvent that is intended to fluidize said cosmetic product.

This volatile solvent is not intended to remain on the keratin fibres to which the cosmetic product has been applied. The volatile solvent evaporates from the product during a drying phase.

In the case of mascaras, the most frequently used solvents comprise notably water and isododecane, the latter being generally used in waterproof mascaras.

The cosmetic product is applied by means of an applicator. Numerous cosmetic product applicators that are intended to apply said product to keratin fibres, in particular to apply mascara to eyelashes, are known.

Generally, an applicator comprises a, generally elongate, main body, said main body bearing protruding application elements.

During application, the applicator is loaded with cosmetic product and brought into contact with the fibres in order to deposit the product on said fibres.

In practice, the solvent evaporates as soon as the cosmetic product is exposed to the air, that is to say as soon as the container is opened and the applicator bearing the product to be applied is withdrawn. As a result, the drying phase takes place at the same time as the application phase.

The time for which the cosmetic product remains sufficiently fluid to be applied is denoted "playtime" or application time.

This application time depends notably on the volatility of the solvent used and on the configuration of the applicator member, it being possible for the product loaded on the application elements to be exposed to the air to a greater or lesser extent during application.

The application time is particularly important, notably as regards ease of use.

In particular, a long application time allows a user to take more time to apply her make up without having to dip the applicator back into the reservoir several times.

A long application time also makes it possible to limit the formation of lumps or clumps of dried product on the applicator member.

There is thus a general need to increase the application time for such a cosmetic product.

This need is all the more important because the applicator member is complex and designed to produce different effects on the eyelashes. Specifically, such an applicator member has application elements arranged along the main body in an irregular and specific manner. In particular, it is possible to provide more or less dense regions intended to contain a greater or smaller quantity of product to be applied. These different regions are thus exposed to the ambient air differently and, as a result, can have different application times or "playtimes".

Obviously, the application time for the cosmetic product is determined with respect to the region having the most rapid evaporation (the shortest application time).

One solution for increasing the application time consists in providing a device of the felt-tip-pen type comprising an applicator member having a first end disposed inside a reservoir in contact with the cosmetic product and a second, free, end forming the end for applying the product. In such a device, the cosmetic product propagates by capillary action through the applicator member, which is thus always fed with fresh cosmetic product comprising a sufficient proportion of solvent necessary for its application.

This type of felt-tip-pen device is not suitable for all cosmetic products, however. This is because some cosmetic products, which are particularly thick, cannot diffuse through such an applicator member. This is particularly true for mascaras.

The present invention aims to achieve these objectives and to this end proposes an assembly for packaging and applying a cosmetic product comprising at least one volatile solvent, said packaging and application assembly comprising, for the one part, a body forming a reservoir which is intended to contain the cosmetic product to be applied and a free edge of which delimits an opening, said body being equipped with a closing member provided to close the opening of said reservoir in a removable manner, and, for the other part, an applicator comprising an applicator member having an elongate main body bearing a set of protruding application elements that define between one another a plurality of spaces for loading and applying the cosmetic product, said applicator being able to move between a first position, known as the pick-up position, in which the applicator member is situated inside the reservoir and is able to be brought at least partially into contact with the cosmetic product intended to be contained in the reservoir, and a position, known as the application position, in which the applicator member can be brought into contact with a part of the human body, said packaging and application assembly being characterized in that at least some of the spaces for loading and applying cosmetic product are delimited by at least one surface produced from an open-cell porous material that can selectively absorb some of the volatile solvent of the cosmetic product.

A porous material that can selectively absorb some of the volatile solvent of the cosmetic product is understood as being a material which, when brought into contact with the cosmetic product, absorbs mainly and preferentially said solvent with respect to the active components of the cosmetic product. Of course, a small quantity of the active components is likely to be absorbed all the same.

According to the present application, absorption of the solvent is considered to be selective when the ratio between the mass concentration of the solvent in the formula and the mass concentration of the solvent in the porous material is greater than 1.3, preferably greater than 1.5, even more preferably greater than 1.75, or even greater than 1.9.

Thus, for a cosmetic product comprising 50% by weight of solvent, absorption is considered to be selective if the concentration of solvent in the liquid absorbed is greater than 65% (65%/50%>1.3).

Thus, by providing a free surface situated in the vicinity of at least some of the application elements and produced from an open-cell porous material that can selectively absorb some of the volatile solvent of the cosmetic product, the applicator member, when it is in the closed position dipped into the cosmetic product, absorbs and becomes loaded essentially with solvent of the cosmetic product. The active components, such as waxes and film-forming components, intended to remain on the part of the user's body, are not notably absorbed. These active components thus remain easily available for application.

During application, it was surprisingly found that the application time thereof was greatly increased.

Without wishing to be bound by any theory, the applicant believes that the porous material loaded with solvent progressively releases said solvent at the loading and application space, thereby making it possible to compensate to a certain extent for the losses of solvent from the cosmetic product by evaporation.

More specifically, the solvent evaporating from the porous material helps to maintain a partial solvent pressure at the loading and application space, thereby limiting the evaporation of solvent from the product. Additionally, when the cosmetic product loaded is in contact with the porous material, solvent can be diffused from said porous material in order to compensate for losses of solvent from the product and thereby to limit the drop in concentration of said solvent in the cosmetic product.

Preferably, the applicator is connected to the closing member of the reservoir.

Advantageously, the reservoir has a wiping member, disposed close to the opening, that is able to wipe at least the applicator member of the applicator as the applicator is withdrawn.

According to one preferred embodiment, the open-cell porous material that can selectively absorb some of the volatile solvent of the cosmetic product is a felt, notably a felt produced from fibres chosen from nylon, polyesters, polyacrylics, polyolefins, SEBS, polyamides and polyacetals.

Advantageously, at least some of the application elements are produced from the open-cell porous material that can selectively absorb some of the volatile solvent of the cosmetic product. Thus, by producing application elements from the porous material, the cosmetic product loaded is in direct contact with the solvent exchange surface, thereby further improving the application time.

According to one particular embodiment, the main body of the applicator member is produced from the open-cell porous material that can selectively absorb some of the volatile solvent of the cosmetic product. Thus, by producing the main body from the porous material, it is possible to store a large quantity of solvent in said body. Moreover, the solvent can diffuse through the porous material along a significant length of the main body. This results in better distribution and diffusion of the solvent depending on the application.

Advantageously, the application elements are produced in one piece with the main body, and notably are machined into the main body of the applicator member. It is also possible to mould the application elements.

Alternatively, the application elements are carried by a perforated holder forming a sleeve, inside which the open-cell porous material that can selectively absorb some of the volatile solvent of the cosmetic product is disposed. In particular, the application elements can thus be easily made of plastics material, for example.

Preferably, the holes in the support are disposed at a root of the application elements.

According to another particular embodiment, the main body is produced from two strands that are twisted together, at least some of the application elements being clamped between the two strands. In particular, the application elements could notably comprise bristles or filaments.

Preferably, the cosmetic product is chosen from mascaras, glosses, nail varnishes and foundations.

The present invention also relates to a method for applying a cosmetic product, notably a mascara, to keratin fibres, in particular to eyelashes or eyebrows, comprising:
  the provision of a packaging and application assembly according to the invention, comprising the cosmetic product,
  the at least partial immersion of the applicator member in said cosmetic product for a sufficient time for the open-cell porous material that can selectively absorb some of the volatile solvent of the cosmetic product to become loaded with said solvent,
  the opening of the packaging and application assembly and the removal of the applicator member from the reservoir,
  the application of the cosmetic product to a part of the human body, in particular to keratin fibres such as eyelashes or eyebrows, with the aid of the applicator member.

Preferably, the immersion time of the applicator member in the cosmetic product is sufficient to saturate the porous material with solvent.

The present invention will be understood better from reading the following detailed description with regard to the appended drawing, in which:

FIG. 1 is a schematic depiction of a packaging and application assembly according to a first embodiment, the applicator member being in the closed configuration.

FIG. 2 is a schematic depiction of the packaging and application assembly from FIG. 1 in the application configuration.

Figure 5A:
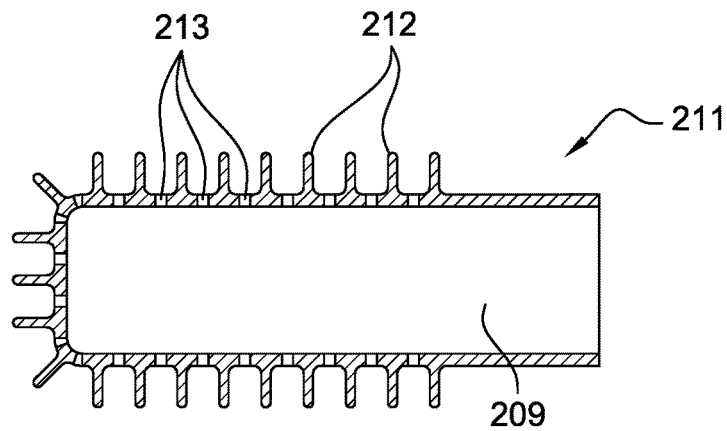
Figure 5B:
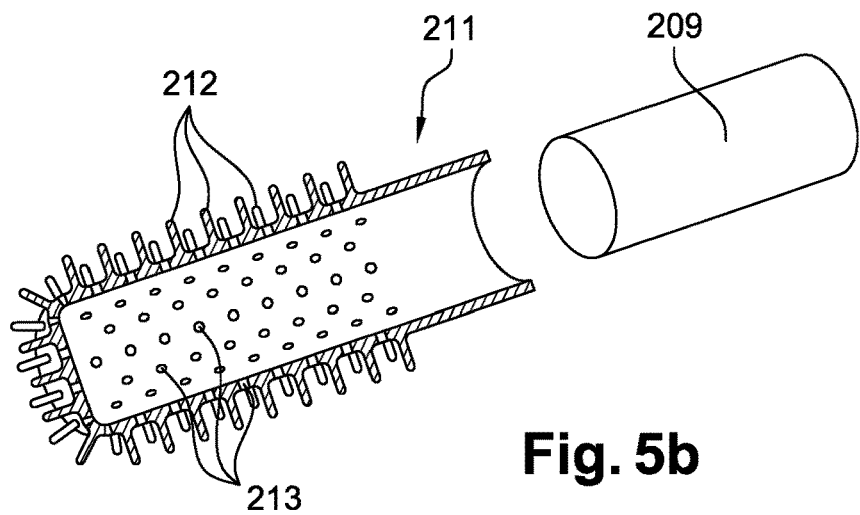

FIGS. 5*a*, 5*b*; 6; 7*a* to 7*b*; 8 to 11 illustrate further variant embodiments.

Figure 12A:
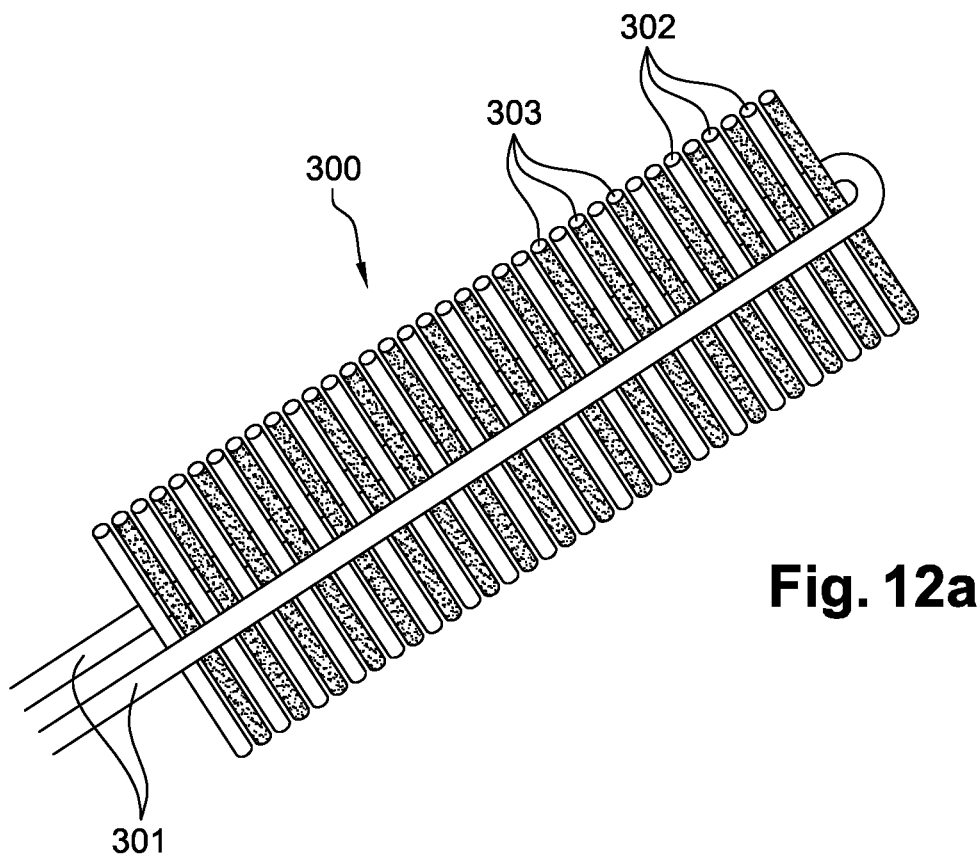
Figure 12B:
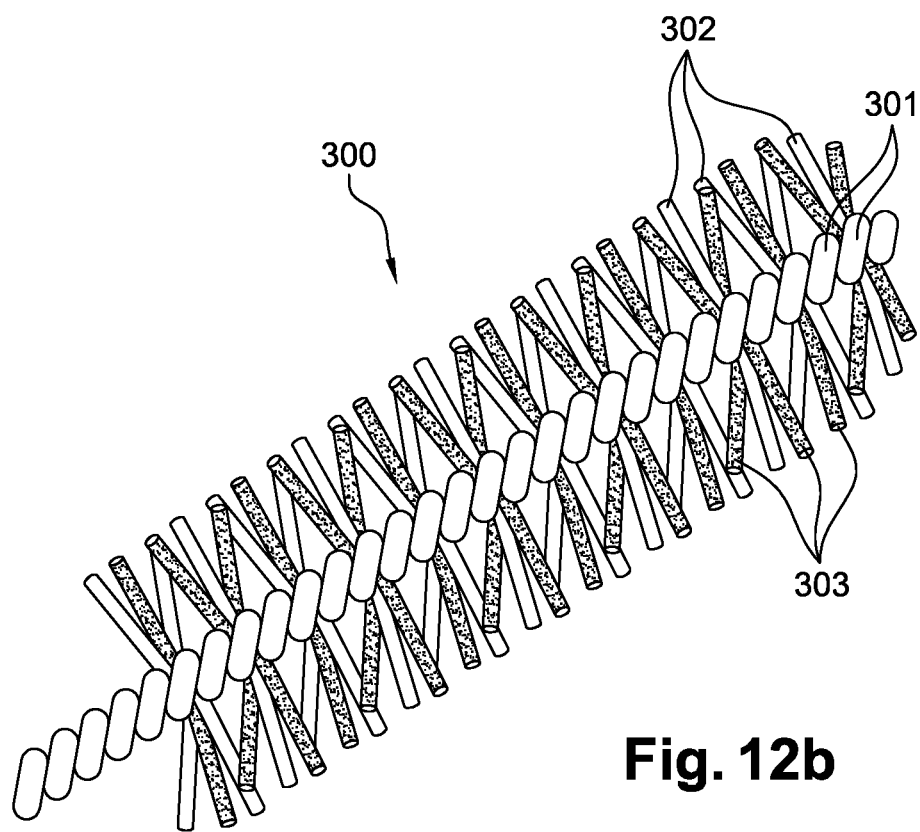

FIGS. 12*a*, 12*b* illustrate an embodiment of the twisted-core brush type.

FIGS. 1 and 2 show an assembly 1 for packaging and applying a cosmetic product P comprising at least one volatile solvent S.

More specifically, the cosmetic product P comprises a set of components that are intended to be applied to a part of the human body and make up the formula F. These components comprise notably waxes and film-forming agents.

The set of components of the formula F is packaged in the presence of a volatile solvent S. In this case, the packaging and application assembly 1 is intended to contain a mascara packaged in an aqueous or organic solvent.

The packaging and application assembly 1 comprises a body forming a reservoir 10 which is intended to contain the cosmetic product P and a free edge 11 of which delimits an opening 12. More specifically, the opening 12 is situated at one end of a neck 13 of the reservoir 10.

The reservoir 10 is equipped with a detachable closing member 14 provided to close the opening 12 of said reservoir 10 in a removable manner. In this case, the closing member 14 is in the form of a cap that is able to engage with the neck 13.

According to the embodiment depicted, the cap 14 comprises an internal seal 15 and forms a sleeve or sheath complementary to the neck 13. Alternatively, a screw cap having an internal thread that is able to engage with an external thread on the neck 13 could conventionally be provided.

The packaging and application assembly 1 comprises an applicator 20 having a stem 21 that has a first end connected to the closing member 14 and a second end connected to an applicator member 22.

The closing member 14 forms a member for gripping the applicator 20.

The applicator member 22 comprises an elongate main body 23 bearing a set of protruding application elements 24. The application elements 24 define between one another a plurality of spaces 25 for loading and applying the cosmetic product P.

By way of the closing member 14, the applicator 20 is able to move between a first position, known as the pick-up position (FIG. 1), in which the applicator member 22 is situated inside the reservoir 10 and is able to be brought at least partially into contact with the cosmetic product P, and a second position, known as the application position (FIG. 2), in which the applicator member 22 can be brought into contact with a part of the human body.

Additionally, the reservoir 10 is equipped with a wiping member 16 that is disposed close to the opening 12 and is able to wipe at least the applicator member 22 of the applicator 20 as the applicator 20 is withdrawn. More particularly, the wiping member 16 is disposed inside the neck 13.

In accordance with the present application, the spaces 25 for loading and applying cosmetic product P are delimited by at least one surface produced from an open-cell porous material that can selectively absorb some of the volatile solvent of the cosmetic product.

According to the embodiment schematically depicted in FIGS. 1 and 2, the applicator member 22 is made of an open-cell porous material that can selectively absorb some of the volatile solvent S.

More particularly, the applicator member 22 is in the form of a stem or baton of said material forming the elongate main body 23, into which the application elements 24 are machined.

Alternatively, the application elements may be obtained by moulding, compression or by any other known technique.

In this case, the application elements 24 are in the form of peripheral teeth alternating with recesses that form the loading and application spaces 25.

The application elements 24 are thus in one piece with the main body 23.

The main body 23 of the applicator member 22 is thus at least partially, or entirely, constituted of said open-cell porous material that can selectively absorb some of the volatile solvent of the cosmetic product.

The application elements 24 are thus also constituted at least partially, or entirely, of said open-cell porous material that can selectively absorb some of the volatile solvent of the cosmetic product.

The open-cell porous material that can selectively absorb some of the volatile solvent of the cosmetic product is a felt, notably a felt produced from fibres chosen from nylon, polyesters, polyacrylics, polyolefins, SEBS, polyamides, polyacetals, or a mixture thereof.

The principle of use of the packaging and application assembly 1 is as follows.

In the closed position, the cap 14 is connected to the neck 13 and closes the reservoir 10. The applicator member 22 is situated inside the reservoir 10 and dips at least partially into the cosmetic product P.

During this immersion, the open-cell porous material that can selectively absorb some of the volatile solvent of the cosmetic product is in at least partial contact with the cosmetic product. Said porous material thus preferably absorbs some of the solvent and becomes loaded with said solvent, possibly until saturated, depending on the immersion time.

During immersion, the loading and application spaces 25 also fill with cosmetic product P to be applied, notably of formula F.

In order to carry out application, the user opens the packaging and application assembly by removing the cap 14 and withdraws the applicator 22.

During withdrawal, the applicator 22 passes through the wiper 16, which removes the excess cosmetic product. The cosmetic product P is retained mainly in the loading and application spaces 25.

The user can then apply the cosmetic product P, notably to her eyelashes, by passing said eyelashes between the application elements 24.

As indicated above, from the moment the reservoir is opened and during application, the solvent evaporates and the cosmetic product P loaded in the loading and application spaces 25 dries out. The presence of solvent S in the porous material thus makes it possible to form a reserve of solvent S for limiting the drying out of said cosmetic product on the application elements 24.

This makes it possible to greatly increase the number of application passages that are possible before the formula F of cosmetic product P dries out too much. The application time or "playtime" is significantly increased thereby.

Figure 3:
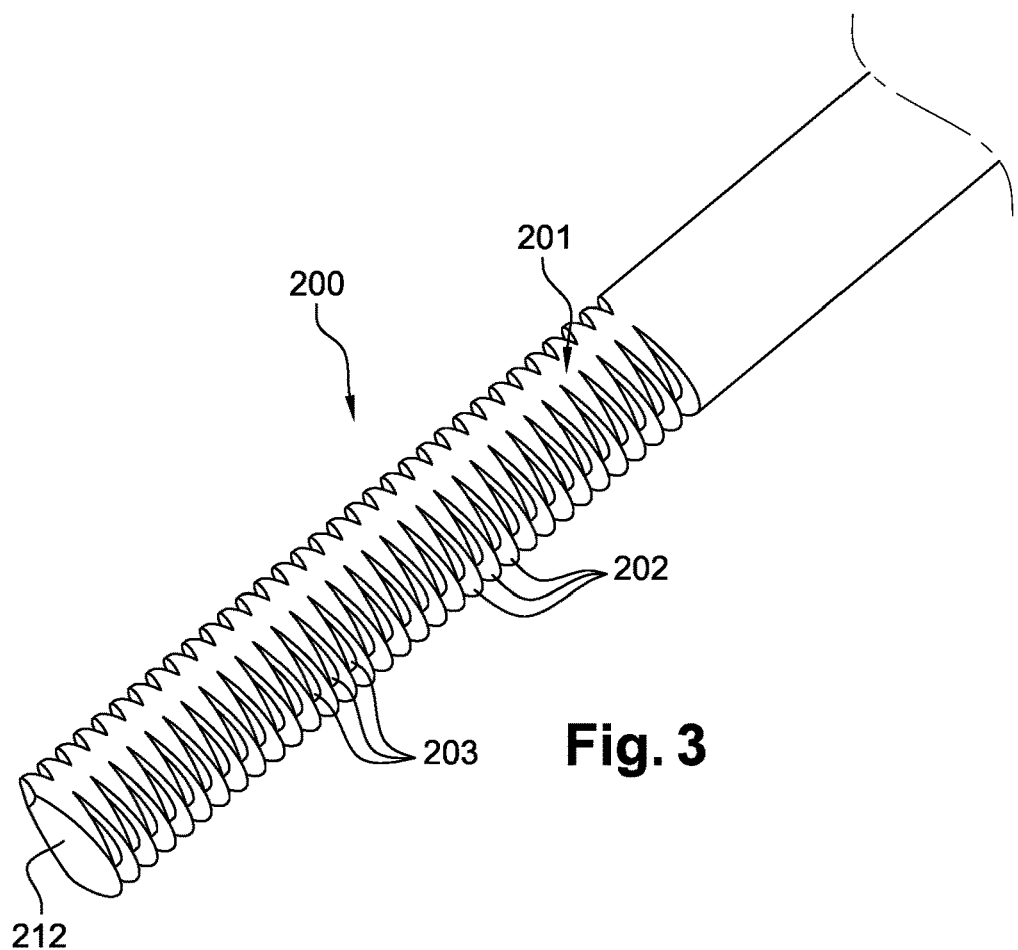
FIG. 3 is a depiction of a variant embodiment of an applicator for a packaging and application assembly according to the invention.
Figure 4:
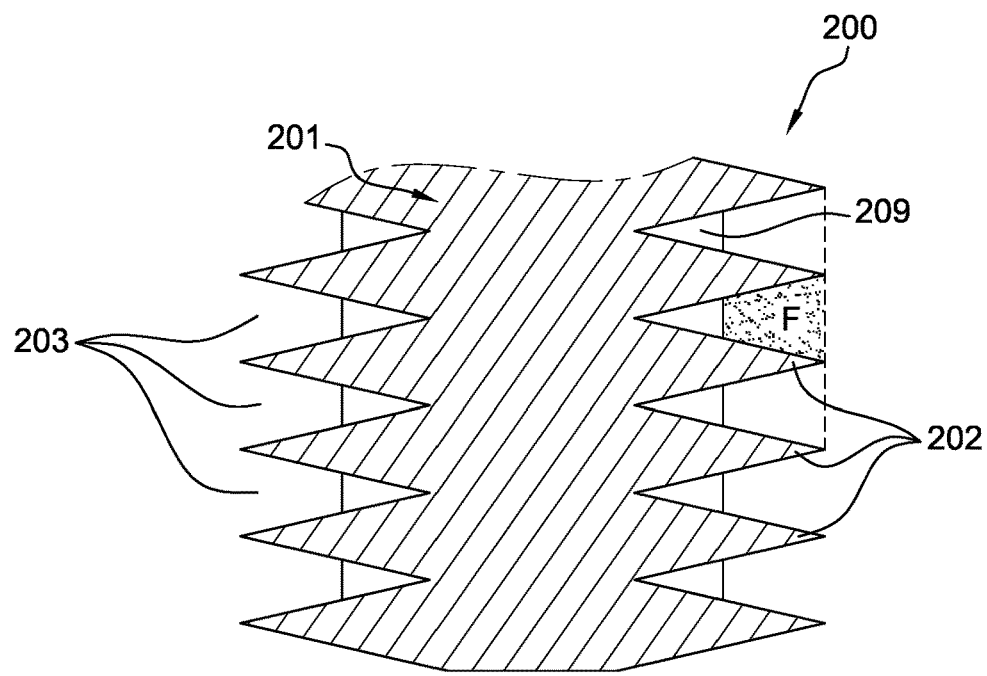
FIG. 4 is an enlarged partial schematic depiction of the applicator from FIG. 3.

FIGS. 3 and 4 show a variant embodiment of the applicator member.

The applicator member 200 is produced in the form of a holder 201 forming a sleeve. In this case, the holder 201 is a sleeve with a cylindrical cross section. Other cross sections are conceivable for the sleeve, notably triangular, oval, etc.

The sleeve is intended to receive a baton 209 with a corresponding shape made of the open-cell porous material that can selectively absorb some of the volatile solvent of the cosmetic product.

The holder 201 is perforated so as to define a set of teeth 202 forming application elements. The holder 201 thus forms an application comb.

More specifically, the teeth 202 are partially peripheral and are disposed in at least one longitudinal row of parallel teeth. In this case, the teeth 202 are disposed in two diametrically opposed longitudinal rows.

The spaces between the teeth therefore define, with at least one opening 203 in the support, spaces for loading and applying the cosmetic product P.

Each opening 203 frees up, at the roots of the teeth 202, a surface of the porous material disposed inside the holder 201. This surface forms a surface for exchange, absorption and release of the solvent S intended to be loaded in said porous material.

The holder 201/sleeve has a closed distal end 212. Alternatively, the distal end may be open, thereby freeing up an additional loading surface.

FIGS. 5a to 5b, 6 and 7a to 7b show several variants of the holder forming a sleeve.

FIGS. 5a and 5b show a holder 211 forming a sleeve bearing a set of spikes 212 that form application elements. Between said spikes 212, through-orifices 213 that free up access to the baton of porous material 209 disposed inside the holder 211 are formed.

Figure 6:
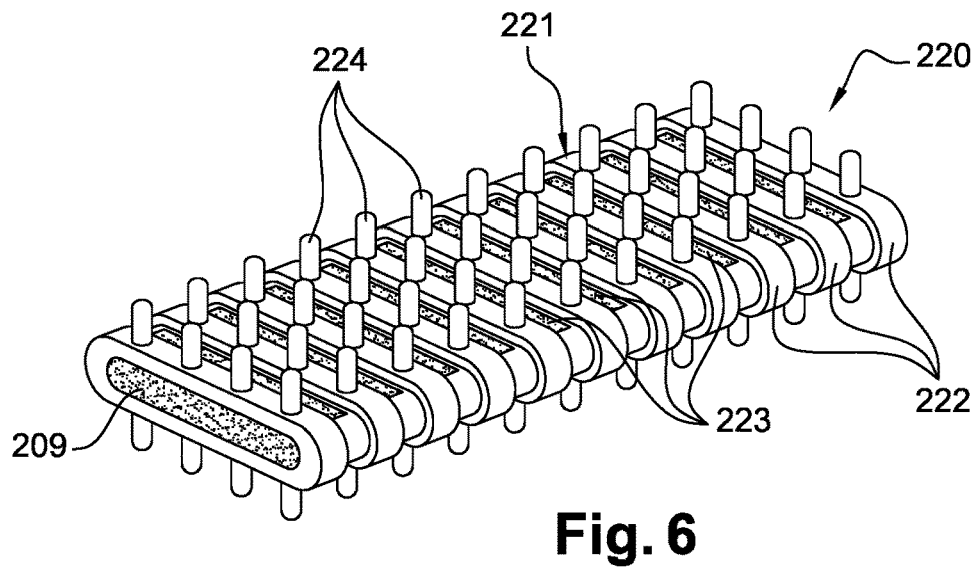

FIG. 6 shows an applicator member 220 comprising a holder 221 having a set of peripheral ribs 222 distributed along said holder 221. Preferably, the ribs 222 are substantially parallel to one another. Openings 223 are formed in the holder 221 between the peripheral ribs 222.

Additionally, the ribs 222 bear one or more spikes 224.

In this case, the holder 221 has a generally oval cross section having two substantially flattened opposed faces. The spikes 224 are disposed on the flattened sides, in particular on each flattened face.

Figure 7A:
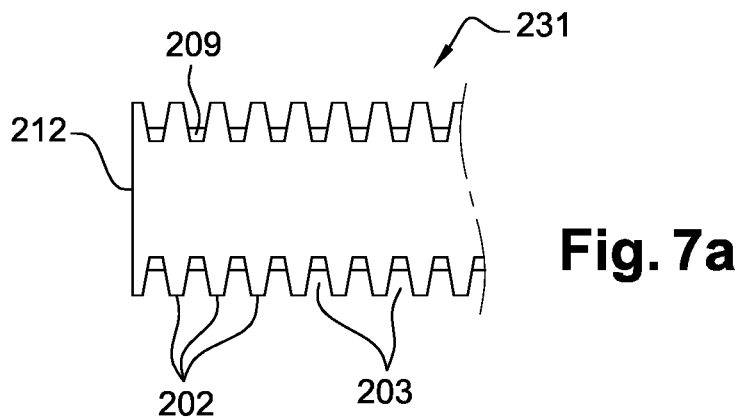
Figure 7B:
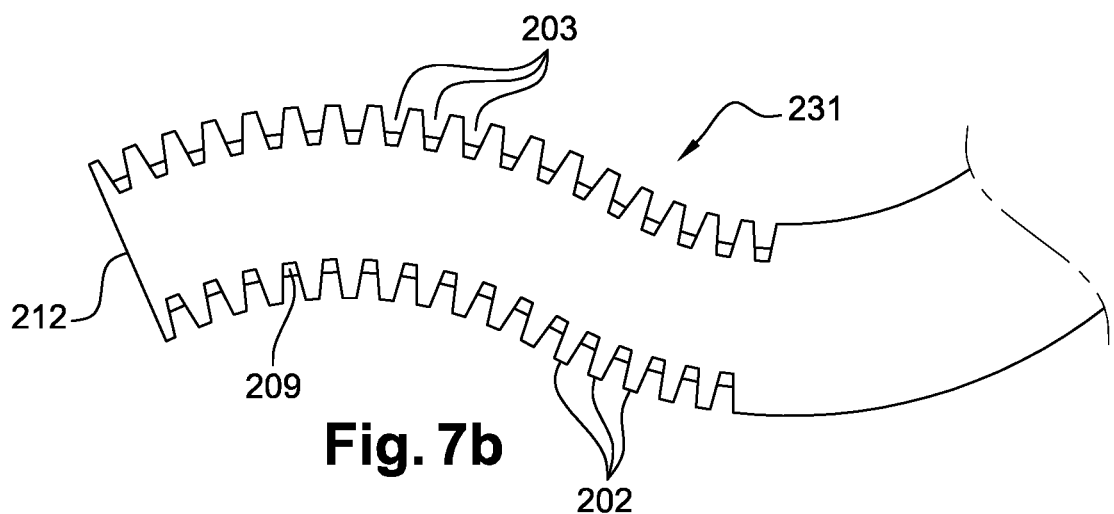

FIGS. 7a and 7b show a holder 231 similar to the holder 201, except that the holder 231 has an oval cross section.

According to FIG. 7b, the holder 231, and possibly the associated stem, can have one or more curves in a longitudinal direction.

Figure 8:
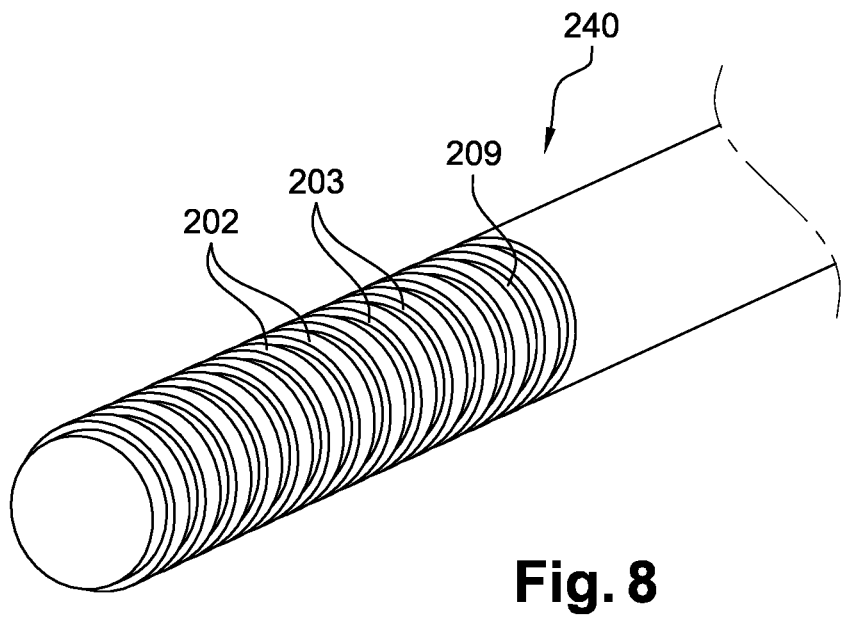
Figure 9:
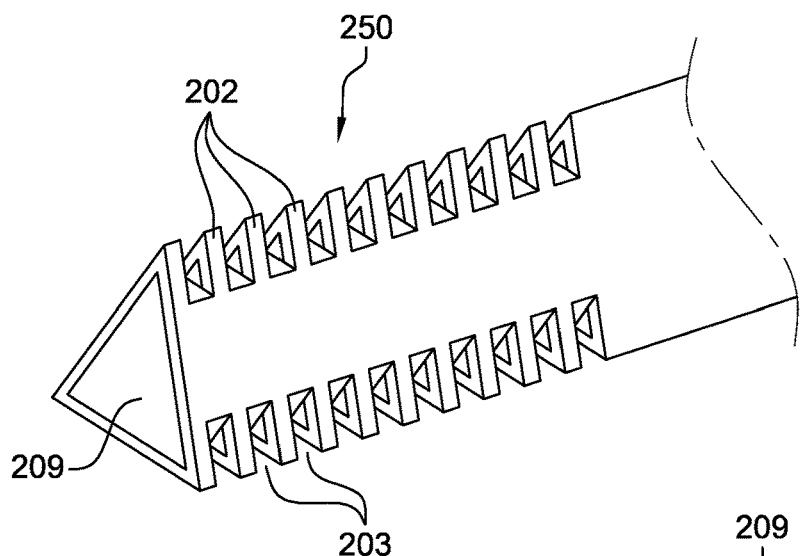

FIGS. 8 and 9 show holders 240, 250 that have respectively circular and triangular cross sections.

Figure 10:
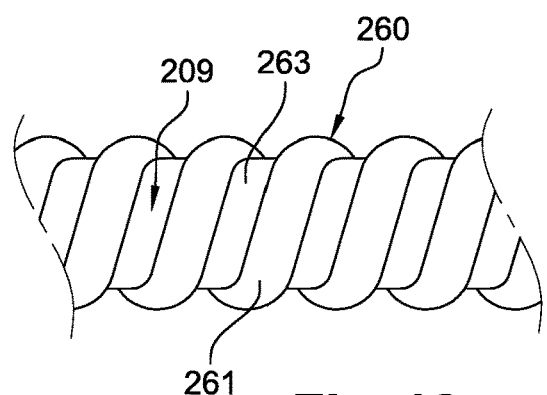

FIG. 10 shows a helical holder 260. More specifically, the holder 260 forms a helical rib 261 and has a similarly helical opening 263. The helical opening frees up a substantially continuous surface for access to the baton of porous material 209 along the length of the applicator member.

In a variant, the opening can be in the form of one or more longitudinal grooves.

Figure 11:
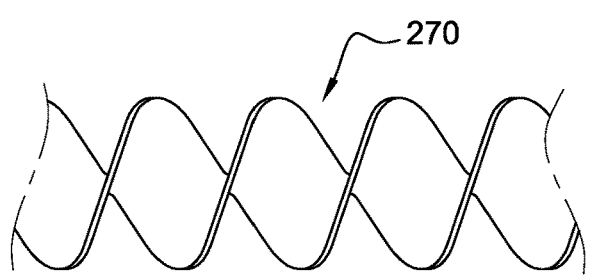
Figure 11:
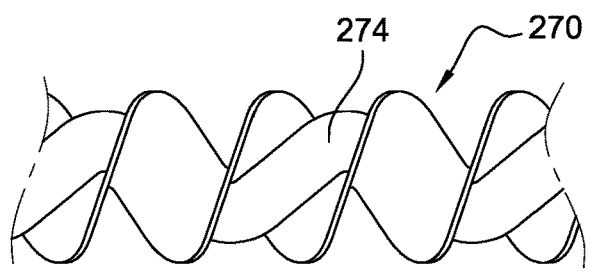
Figure 11:
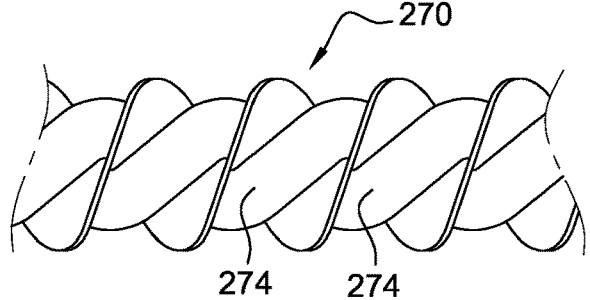

FIG. 11 shows yet another holder 270 in the form of a helix on which one or more batons 274 of porous material are twisted.

The characteristics of the different supports are clearly able to be combined with one another, if necessary.

The holders, and in particular the openings, can be made by any acceptable method, notably by impression (e.g. in the hot state, in relief); by chemical etching, laser, engraving, or heat treatment.

Preferably, the holders are made of plastics material, notably of a thermoplastic material. Alternatively, the holder can also be made of metal, for example aluminium, steel, stainless steel, in order notably to protect said holder from corrosion.

In particular, the holders can be obtained by moulding, overmoulding, extrusion or coextrusion, stamping or machining.

FIGS. 12a and 12b show another embodiment of an applicator member according to the invention.

The applicator member 300 is made in a similar manner to a twisted-core brush. Such a brush is generally produced from two strands 301, notably metal strands, between which a set of fibres or bristles 302 are disposed, said bristles being clamped by twisting the two strands 301 together.

In this case, the two strands 301 are obtained from a single wire folded on itself in a U shape.

The bristles 302 are generally synthetic fibres, notably nylon, which are not specifically absorbent. The bristles 302 form application elements and define between one another spaces for loading and applying the cosmetic product P.

In accordance with the present application, the porous material is produced in the form of filaments 303. The filaments are disposed between the strands 301, between the bristles 302. More particularly, the filaments are disposed in alternation with the bristles 302. Of course, the filaments 303 can be disposed in some other way and notably alternate with sets of several bristles 302.

In this case, the filaments thus also form application elements. Of course, the brush can also only comprise filaments 303.

The filaments 303 are in particular filaments of felt, notably felt made of the abovementioned materials.

The invention claimed is:

1. A packaging and applying assembly for a cosmetic product, comprising:
at least one volatile solvent that includes water and isododecane, said packaging and application assembly comprising, for one part, a body forming a reservoir which contains mascara as the cosmetic product to be applied and a free edge of which delimits an opening, said body being equipped with a closing member provided to close the opening of said reservoir in a removable manner, and, for another part, an applicator comprising an applicator member having an elongate main body bearing a set of protruding application elements that define between one another a plurality of spaces for loading and applying the cosmetic product, said applicator being able to move between a first position, known as the pick-up position, in which the applicator member is situated inside the reservoir and is able to be brought at least partially into contact with the cosmetic product intended to be contained in the reservoir, and a position, known as the application position, in which the applicator member can be brought into contact with a part of the human body, said packaging and application assembly being characterized in that the plurality of spaces for loading and applying cosmetic product are delimited by at least one surface produced from an open-cell porous material, which homogenously makes up both the elongate main body and the protruding application elements and is a felt produced from fibers chosen from one of nylon, polyesters, polyacrylics, polyolefins, SEBS, polyamides and polyacetals, that can selectively absorb at least a portion of the volatile solvent of the cosmetic product with respect to active components of said cosmetic product so that the total ratio between a mass concentration of the solvent in a formula of the cosmetic product filled within the spaces and the mass concentration of the solvent in the open-cell porous material for all the spaces for loading and applying cosmetic product is greater than 1.3.

2. The packaging and application assembly according to claim 1, characterized in that the applicator is connected to the closing member of the reservoir.

3. The packaging and application assembly according to claim 1, characterized in that the reservoir has a wiping member, disposed close to the opening, that is able to wipe at least the applicator member of the applicator as the applicator is withdrawn.

4. A method for applying a cosmetic product, notably a mascara, to keratin fibres, in particular to eyelashes or eyebrows, comprising:
the provision of a packaging and application assembly according to claim 1, comprising the cosmetic product,
the at least partial immersion of the applicator member in said cosmetic product for a sufficient time for the open-cell porous material that can selectively absorb some of the volatile solvent of the cosmetic product to become loaded with said solvent, the opening of the packaging and application assembly and the removal of the applicator member from the reservoir, the application of the cosmetic product to a part of the human body, in particular to keratin fibres such as eyelashes or eyebrows, with the aid of the applicator member.

5. A method for applying a cosmetic product according to claim 4, characterized in that the immersion time of the applicator member in the cosmetic product is sufficient to saturate the porous material with solvent.

\* \* \* \* \*